(12) United States Patent
Banouskou et al.

(10) Patent No.: US 7,850,715 B2
(45) Date of Patent: Dec. 14, 2010

(54) ORTHOPEDIC IMPLANT APPARATUS

(75) Inventors: Ezzine Banouskou, Villepinte (FR); Jose Gournay, Dammartin en Goele (FR); Douglas N. Baker, Collierville, TN (US); Marco Capote, Memphis, TN (US)

(73) Assignee: Warsaw Orthopedic Inc., Warsaw, IN (US)

( * ) Notice: Subject to any disclaimer, the term of this patent is extended or adjusted under 35 U.S.C. 154(b) by 50 days.

(21) Appl. No.: 11/118,644

(22) Filed: Apr. 29, 2005

(65) Prior Publication Data
US 2006/0247624 A1 Nov. 2, 2006

(51) Int. Cl.
*A61B 17/70* (2006.01)

(52) U.S. Cl. .................................. 606/246; 606/278

(58) Field of Classification Search .................. 606/54, 606/60, 61
See application file for complete search history.

(56) References Cited

U.S. PATENT DOCUMENTS

| | | | |
|---|---|---|---|
| 4,569,338 A | 2/1986 | Edwards | |
| 4,827,918 A | 5/1989 | Olerud | |
| 5,047,029 A * | 9/1991 | Aebi et al. | 606/264 |
| 5,053,034 A | 10/1991 | Olerud | |
| 5,176,680 A | 1/1993 | Vignaud et al. | |
| 5,254,118 A | 10/1993 | Mirkovic | |
| 5,527,314 A | 6/1996 | Brumfield et al. | |
| 5,534,002 A | 7/1996 | Brumfield et al. | |
| 5,562,661 A | 10/1996 | Yoshimi et al. | |
| 5,562,662 A | 10/1996 | Brumfield et al. | |
| 5,885,285 A | 3/1999 | Simonson | |
| 5,938,663 A | 8/1999 | Petreto | |
| 5,947,967 A | 9/1999 | Barker | |
| 6,030,388 A | 2/2000 | Yoshimi et al. | |
| 6,183,473 B1 | 2/2001 | Ashman | |
| 6,210,413 B1 | 4/2001 | Justis et al. | |
| 6,248,104 B1 * | 6/2001 | Chopin et al. | 606/267 |
| 6,248,107 B1 | 6/2001 | Foley et al. | |
| 6,280,445 B1 | 8/2001 | Morrison et al. | |
| 6,482,207 B1 | 11/2002 | Errico | |
| 6,520,962 B1 | 2/2003 | Taylor | |
| 6,562,038 B1 | 5/2003 | Morrison | |
| 6,626,906 B1 | 9/2003 | Young | |
| 6,682,529 B2 * | 1/2004 | Stahurski | 606/301 |
| 6,685,705 B1 | 2/2004 | Taylor | |
| 7,163,538 B2 * | 1/2007 | Altarac et al. | 606/61 |
| 2001/0047173 A1 | 11/2001 | Schlapfer et al. | |
| 2002/0029040 A1 | 3/2002 | Morrison et al. | |
| 2002/0099331 A1 * | 7/2002 | Burchfield | 604/94.01 |
| 2005/0277931 A1 | 12/2005 | Sweeney et al. | |
| 2006/0149245 A1 | 7/2006 | Sweeney et al. | |

FOREIGN PATENT DOCUMENTS

| | | |
|---|---|---|
| DE | 92 15 561 U1 | 1/1993 |
| WO | WO 00/18310 | 4/2000 |
| WO | WO 00/62692 | 10/2000 |
| WO | WO 01/39677 | 6/2001 |
| WO | WO 2005/122965 | 12/2005 |
| WO | 2006119237 A | 11/2006 |

* cited by examiner

*Primary Examiner*—Thomas C Barrett
*Assistant Examiner*—Nicholas Woodall

(57) ABSTRACT

Apparatuses are disclosed for use in orthopedic surgery, for example for procedures in which a support member is connected to the spine. A connector member for connecting to an orthopedic implant and a support member is provided. A sleeve fits around the implant, and a locking member or mechanism connects to the sleeve. Locking causes a part of the sleeve to press the support against the connector, and causes a part of the sleeve to compress around the implant, so that the implant and support are substantially inhibited or prevented from moving with respect to each other.

20 Claims, 5 Drawing Sheets

ORTHOPEDIC IMPLANT APPARATUS

The present disclosure relates to apparatuses useful in orthopedic surgery, and in particular to orthopedic supports and devices useful in connecting them to tissues such as bones (e.g. vertebrae) or bone fragments.

BACKGROUND

Several types of implants, connectors and supports for providing therapeutic or corrective assistance to tissues such as bones or bone fragments toward healing of a trauma or correcting of an abnormality are known. Some such apparatuses are not particularly easy to use or orient in a desired way, or are otherwise deficient in operation. Thus, there remains a need in the art for apparatuses that provide advantages over existing items.

DESCRIPTION OF THE ILLUSTRATED EMBODIMENTS

Figure 2:
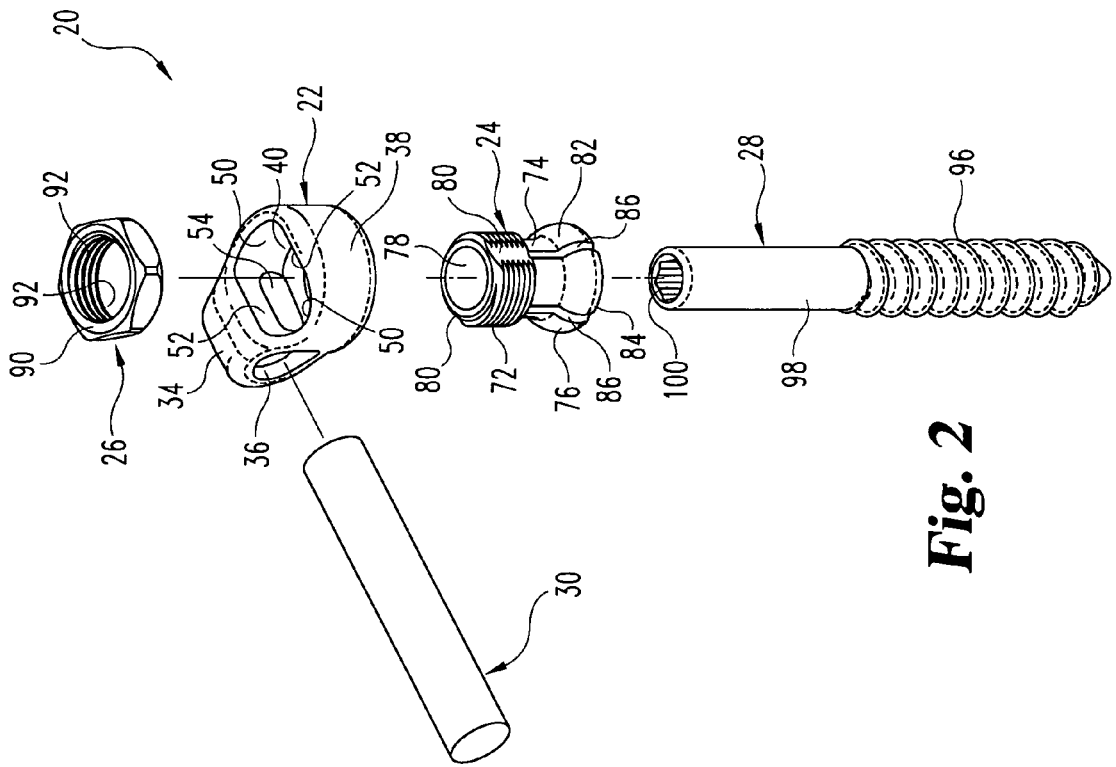
FIG. 2 is an exploded view in perspective of the embodiment shown in FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated, as would normally occur to one skilled in the art to which the invention relates.

Referring now generally to the figures, there are shown embodiments of orthopedic devices useful in supporting bone tissue to promote correction of deformity or abnormality or healing of injury. In one embodiment of an apparatus 20, a connector 22, a sleeve mechanism 24, and a locking mechanism 26 are provided to connect an implant 28 and an elongate member 30.

In one illustrated embodiment, connector 22 is an oblong piece having a first portion 34 with a hole 36, and a second portion 38 with a hole 40. Portions 34 and 38 are side-by-side in that embodiment. Hole 36 has a longitudinal axis along or parallel to which support 30 extends. In a particular embodiment, hole 36 is separated into a substantially cylindrical portion 42 and a second portion 44, which may also be cylindrical. Portions 42 and 44 may be separated by one or more ridges or protrusions 46, which can extend substantially along the whole length of hoe 36. Portion 42 of hole 36 may have a diameter or width substantially the same as or slightly larger than a diameter or width of support 30, and a distance between ridges 46 (or between a ridge 46 and an opposing wall in embodiments having one ridge) may be substantially the same as or slightly smaller than a diameter or width of support 30. Such sizing allows a relatively close or snap fit between support 30 and portion 34 of connector 22.

Hole 40 of connector 22, in an illustrated embodiment, includes substantially cylindrical portions 50 and substantially flat portions 52, giving hole 40 a generally oblong configuration. Holes 40 and 36 overlap or communicate with each other, as at area 54. A part 56 of hole 40 widens as it approaches a surface of connector 22, and in a particular embodiment part 56 has wall portions 58 that are concavely curved. Wall portions 58 could be spherically or parabolically concave, or may be convex in such shapes or others, or could be otherwise configured, for example conical.

In a particular embodiment, the axis of hole 36 is below a plane P that bisects portion 34 and is substantially perpendicular to hole 40. Such a plane P may be perpendicular to a surface 62 and equidistant from surfaces 64 and 66 of portion 38. In that embodiment, more of support 30 will be below plane P than will be above it. A surface 68 of portion 34 in that embodiment may be a greater distance from plane P than surface 66 of portion 38 is from plane P. Surfaces and corners of connector 22 may be rounded.

An illustrated embodiment of sleeve mechanism 24 is a sleeve having a threaded portion 72, a medial portion 74, a bulbous portion 76, and a hole 78 through them. That embodiment of threaded portion 72 includes machine threads and two substantially flat surfaces 80. It will be seen that embodiments of sleeve mechanism 24 may have zero or more such flat surfaces. Where one or more surfaces 80 are provided, they may be configured to be adjacent to surfaces 52 when sleeve mechanism 24 is placed in connector 22. Medial portion 74 is generally cylindrical. In an illustrated embodiment, bulbous portion 76 is substantially pear-shaped, having a first convex part 82 connecting with medial portion 74 and a second convex part 84 that is further distal from threaded portion 72. Convex part 82 curves relatively slowly (e.g. if spherical, the radius of part 82 is relatively large), and convex part 84 curves relatively quickly (e.g. if spherical, the radius is relatively small). One or more slots 86 in medial portion 74 and bulbous portion 76 extend substantially parallel to hole 78. In a particular embodiment, four slots 86 are provided, each separated by about 90 degrees around sleeve mechanism 24.

Locking mechanism 26 is a nut in an illustrated embodiment, having an upper surface 90, a lower surface 92, and a threaded hole 94. Locking mechanism 26 may have an external print, hexagonal in one embodiment, or other structure for accommodating a holding, driving or tightening tool. Lower surface 92 is rounded in an illustrated embodiment, so as to have greater surface contact with embodiments of connector 22 that have a rounded or curved surface around hole 40, to allow locking mechanism 26 to sit relatively lower with respect to connector 22, (e.g. less of locking mechanism 26 extends outside of connector 22), or for other purposes. Threaded hole 94 is for accommodating threaded portion 72 of sleeve mechanism 24. It will be seen that a variety of locking mechanisms could be used depending on the configuration of sleeve mechanism 24. For example, a variety of threaded members could be used if sleeve mechanism 24 is threaded, or if sleeve mechanism 24 is not threaded, other types of locking, holding or clamping members could be used.

Implant 28 is shown in one embodiment as a screw having a threaded bone engagement portion 96 and a connecting portion 98. Engagement portion 96 will have standard cancellous bone threads or other threads adapted to engaging with bone. Connecting portion 98 is substantially cylindrical in that embodiment, and its diameter may be substantially the same as the root diameter of engagement portion 98. In other embodiments of implant 28, a hook, clamp or other bone-engaging structure may be a part of engagement portion 96. Connecting portion 98 may have any of a number of external shapes, and may be smooth, roughened, or otherwise textured. Connecting portion 98 may include a print 100, which is an internal hexagonal print in the above embodiment, for accommodating a holding, gripping or driving tool. It will be seen that print 100 could be otherwise configured, e.g. hexalobed or square, or external.

Support member 30 is a spinal rod in an illustrated embodiment. Various diameters of such rods may be used with connector 22. Various connectors 22 having different diameter holes may be provided in a kit or otherwise to handle a range of rod diameters. Other embodiments of a support member can include non-cylindrical rods or bars, connectors, plate-like members or other structure. Support member 30 is shown as relatively smooth, but may be roughened (as by knurling or threading) or otherwise textured.

Connector 22, sleeve mechanism 24 and locking mechanism 26 may be loosely assembled at or around the time of manufacture, or at another time prior to surgery. Sleeve mechanism 24 is inserted through hole 40 so that a portion of sleeve mechanism 24 extends from surface 64 of connector 22. Locking mechanism 26 is connected to sleeve mechanism 24. In embodiments in which sleeve mechanism 24 and locking mechanism 26 are threaded, locking mechanism 26 is threaded onto sleeve mechanism 24. Locking mechanism 26 is loosely connected to sleeve mechanism 24 so that connector 22, sleeve 24 and locking mechanism 26 can be later adjusted and/or tightened with respect to each other. In one embodiment, one or more connectors 22 can be loaded onto support 30 by inserting support 30 into hole 36 of each such connector 22. Connector(s) 22 can be assembled with respective sleeve(s) 24 and locking mechanism(s) 26 prior to being loaded onto a support 30. Alternatively, connector(s) 22 may be first loaded onto support member 30, and then assembled with respective sleeve(s) 24 and locking mechanism(s) 26.

Use of the illustrated embodiment of apparatus 20 will now be described with reference to a surgical procedure on the spine using bone screws, as an example. Apparatus 20 may be used in a variety of orthopedic treatments, at other surgical sites, and/or with other types of implants. Descriptions of the use of the embodiments herein in the context of spinal surgery, using a spinal rod as support member 30 and a bone screw as implant 28, are not intended to be limiting, as surgery on other tissues may be performed with them, and support members and implants such as those described above may be used additionally or alternatively.

To treat the condition or injury of the patient, the surgeon obtains access to the surgical site in a manner well known in the art, e.g. through incision and retraction of tissues. Access to the surgical site is obtained, e.g. via an opening such as a midline incision above the affected area, with tissue being resected laterally to the transverse process, or by other surgical procedure. The surgeon may connect one or more implants to adjacent or nearby vertebrae that require compression or distraction in order to relieve or improve their condition. For example, pilot holes in vertebrae, e.g. in pedicles, may be made, and screws may be inserted into or otherwise connected to two or more vertebrae.

Figure 1:
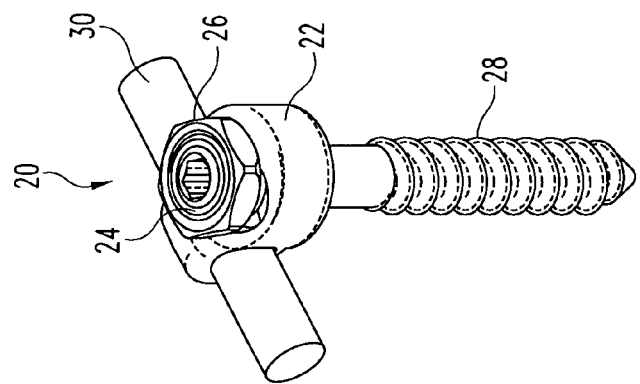
FIG. 1 is a perspective view of an embodiment of apparatus useful in orthopedic surgery.
Figure 4:
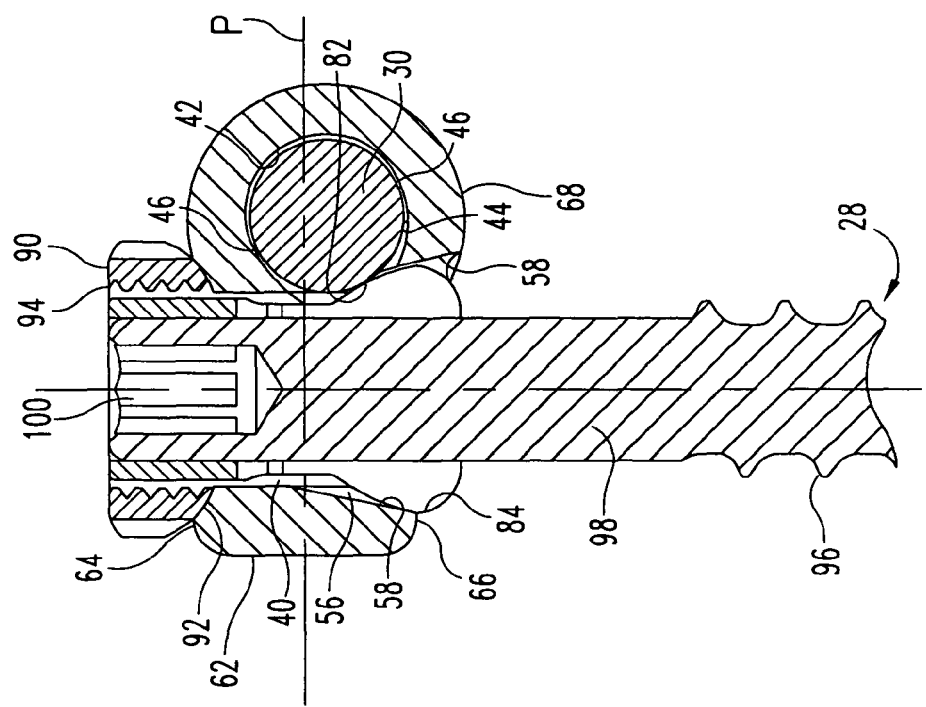
FIG. 4 is a cross-sectional view of the structure shown in FIG. 3, taken along the lines 4-4 in FIG. 3 and viewed in the direction of the arrows.
Figure 3:
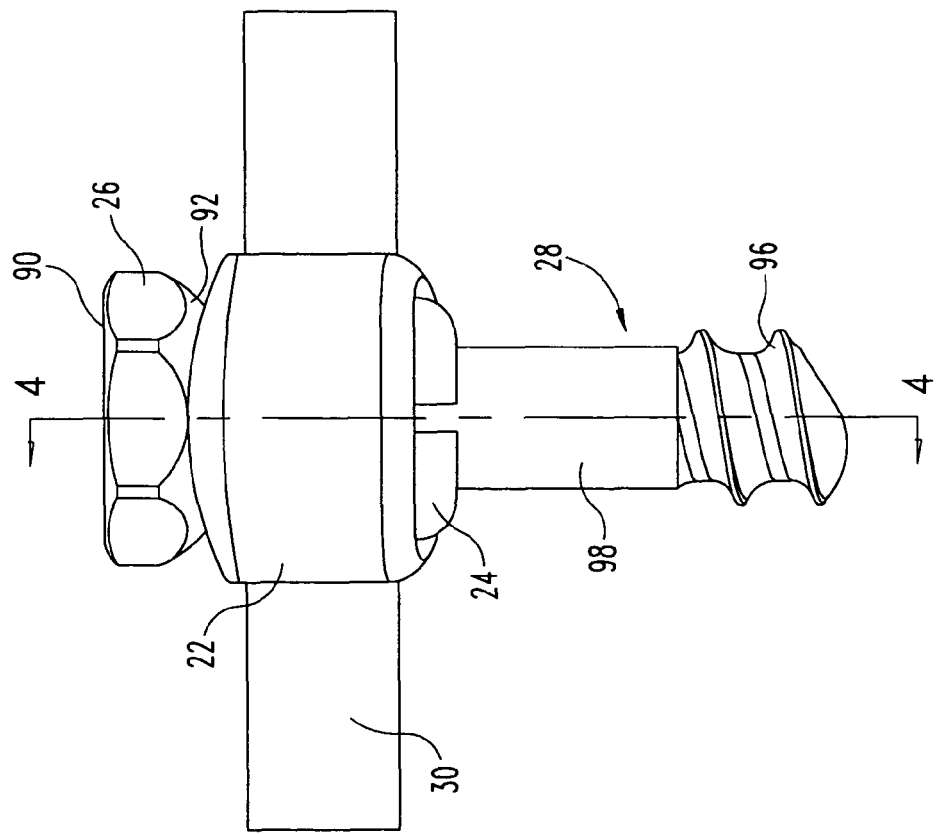
FIG. 3 is a front view of the embodiment shown in FIG. 1.

Once such implant(s) (e.g. implants 28) are placed as desired, the surgeon can move support member 30 into position adjacent the implants. An implant such as implant 28 can be connected to support member 30 via a connector 22 with a sleeve 24 and locking mechanism 26 loaded thereon. Support member 30 is maneuvered to a position adjacent implant 28, and connector 22 is moved along support 30 so that its hole 40 and hole 78 of sleeve mechanism 24 is adjacent implant 28. Connector 22 is placed over implant 28, so that at least a portion of implant 28 is inside hole 78 of sleeve mechanism 24. A portion of implant 28 may also be within hole 40 of connector 28. Connector 22, with sleeve 24 and locking mechanism 26, can be moved along implant 28 to the degree desired by the surgeon. Implant 28 can extend somewhat from sleeve 24 and/or locking mechanism 26, or can be substantially level with sleeve 24 and/or locking mechanism 26 (as in FIG. 1), or can be lower than sleeve 24 and/or locking mechanism 26, depending on how distant the surgeon wishes connector 22 and support member 30 to be from bone tissue.

When connector 22 is positioned with respect to implant 28 as desired, the surgeon than locks the construct. In the embodiment in which locking mechanism 26 is a nut, it is tightened on sleeve mechanism 24. When locking mechanism 26 contacts connector 22, further tightening causes sleeve mechanism 24 to be pulled through hole 40, so that bulbous portion 76 contacts support 30. In an illustrated embodiment, convex part 82 of sleeve 24 contacts support member 30 and presses it against section 42 of connector 22. Tightening also causes compression of sleeve mechanism 24 around implant 28 as a reaction to pressing support 30 against connector 22. Apparatus 20 is locked when locking mechanism 26 causes sleeve mechanism 24 to press support 30 against connector 22, with sleeve mechanism 24 being compressed against implant 28. In a locked condition, sleeve 24 is pressed against implant 28 so that relative movement between them is prevented or substantially inhibited, and support 30 is pressed against connector 22 so that relative movement between them is prevented or substantially inhibited.

Figure 5:
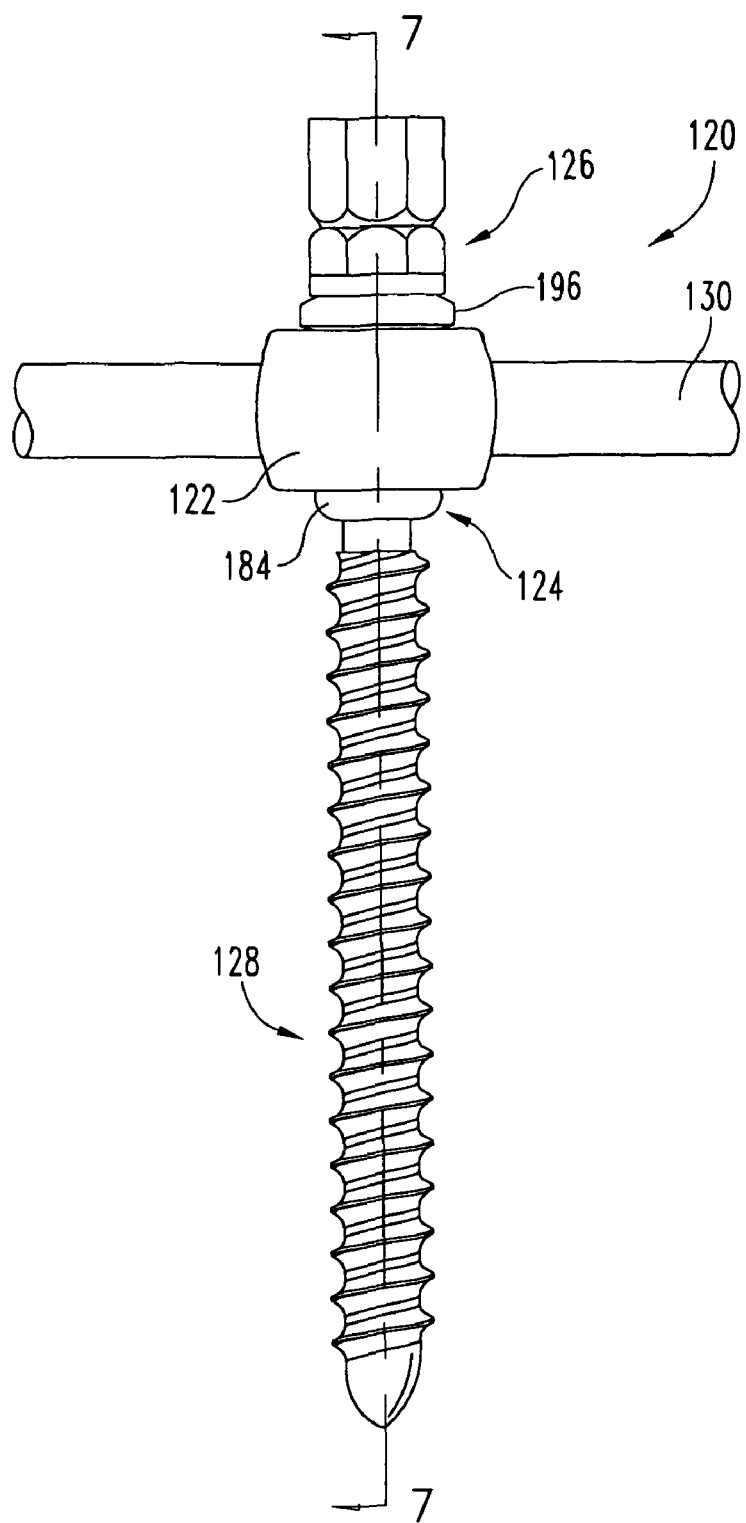
FIG. 5 is a front view of another embodiment of apparatus useful in orthopedic surgery.
Figure 6:
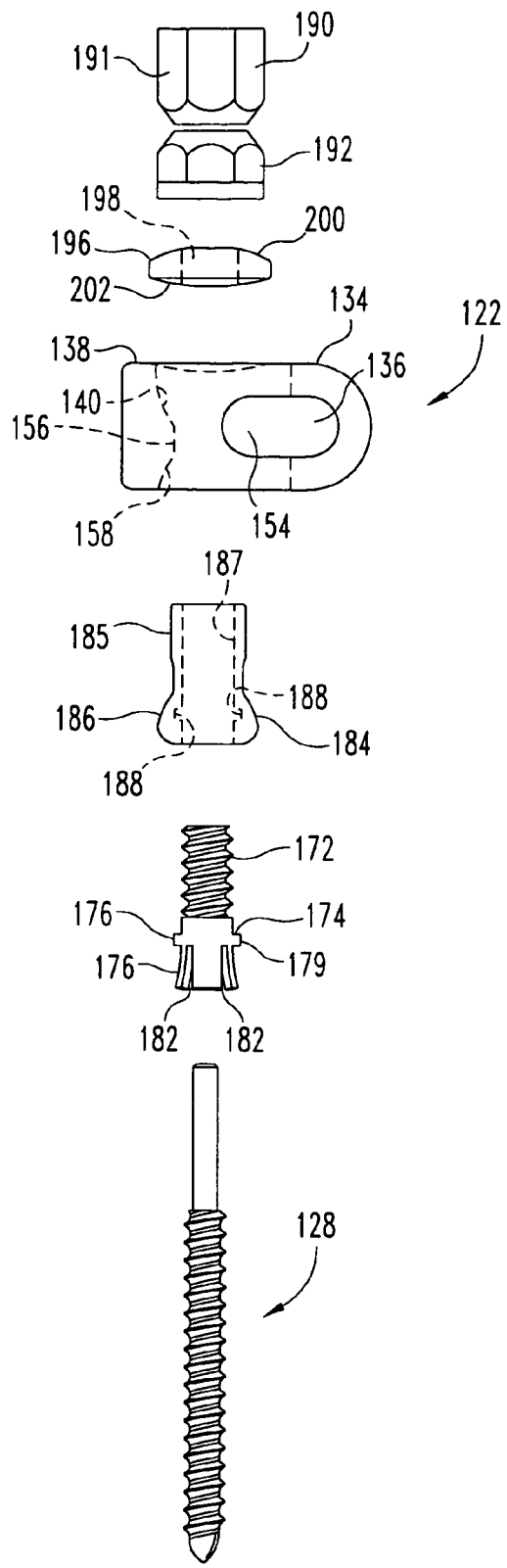
FIG. 6 is a side exploded view of the structure shown in FIG. 5.
Figure 7:
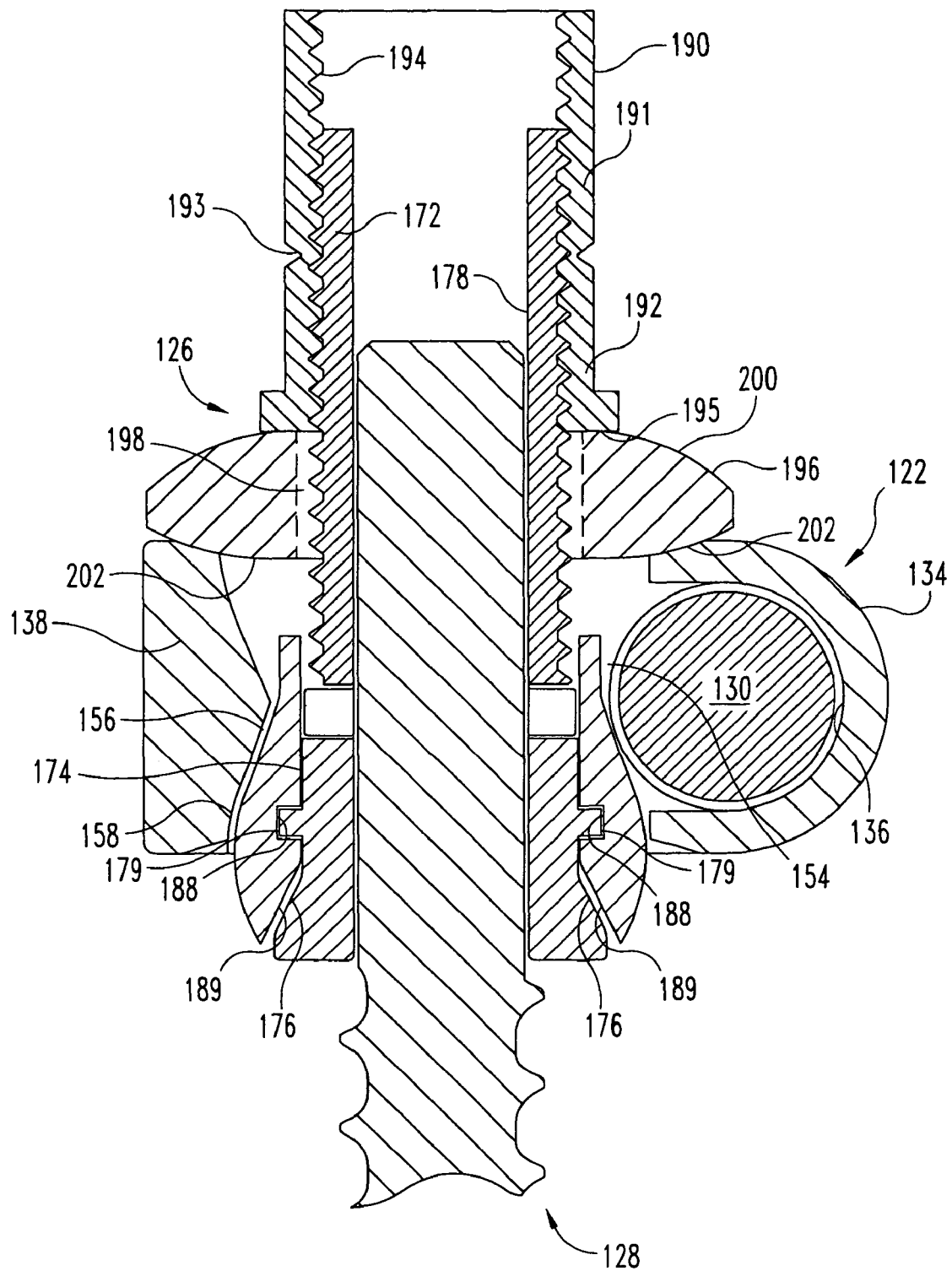
FIG. 7 is a cross-sectional view of the structure shown in FIG. 5, taken along the lines 7-7 in FIG. 5 and viewed in the direction of the arrows.

Turning now to FIGS. 5-7, there are shown other embodiments of orthopedic devices. Apparatus 120 includes a connector 122, a sleeve mechanism 124, a locking mechanism 126, an implant 128 and a support member 130. These components can connect together to provide support to injured or deformed bone tissue.

Connector 122 is an oblong block in an illustrated embodiment, having a first portion 134 with a hole 136 and a second portion 138 with a hole 140. Portions 134 and 138 are side-by-side in that embodiment. Hole 136 is oblong and has an axis along or substantially parallel to which support 130 extends. Hole 140 of connector 122, in an illustrated embodiment, has a generally oblong configuration with a long dimension substantially perpendicular to the axis of hole 136. Holes 140 and 136 overlap or communicate with each other, as at area 154. A part 156 of hole 140 widens as it approaches a surface of connector 122, and in a particular embodiment part 156 has wall portions 158 that are concavely curved. Wall portions 158 could be spherically or parabolically concave, or may be convex in such shapes or others, or could be otherwise configured, for example conical.

An illustrated embodiment of sleeve mechanism 124 includes a sleeve having a threaded portion 172, a medial portion 174, a widened portion 176, and a hole 178 through them. That embodiment of threaded portion 172 includes machine threads. Medial portion 174 is generally cylindrical in the illustrated embodiment. One or more bosses or protrusions 179 are provided, and may be placed on medial portion 174 or at or adjacent the junction between medial portion 174 and widened portion 176. Protrusion(s) 179 may be individual extensions, such as square or cylindrical extensions substantially perpendicular to hole 178, or may be a ridge or flange that is substantially annular, e.g. extending around substantially the entire circumference of sleeve 124. In an illustrated embodiment, widened portion 176 is substantially pear-shaped or conically flared. In a pear-shaped embodiment, portion 176 may be convex. One or more slots 182 in medial portion 174 and widened portion 176 extend substantially parallel to hole 178. In a particular embodiment, four slots 182 are provided, each separated by about 90 degrees around sleeve mechanism 124.

Sleeve mechanism 124 may also include a bulbous member 184 in an illustrated embodiment. Bulbous member 184 has a substantially cylindrical external portion 185, a substantially spherical external portion 186, and an opening 187 therethrough. Opening 187 has one or more indentations 188, which may be a substantially annular groove, and a widening portion 189. Indentation(s) 188 are sized and configured to accommodate protrusion(s) 179 of sleeve 124. Widening portion 189 may be curved in one embodiment, such as spherically or parabolically concave, or may be convex in such shapes or others, or could be otherwise configured, for example conical.

Locking mechanism 126 includes a locking member 190. Locking member 190 is a break-off nut in an illustrated embodiment, having an upper portion 191, a lower portion 192, a reduced-diameter break area 193, and a threaded hole 194. Locking mechanism 126 may have an external print, hexagonal in one embodiment, or other structure for accommodating a holding, driving or tightening tool. Lower portion 192 has a rounded lower surface 195 in an illustrated embodiment, so as to have greater surface contact with embodiments of connector 122 that have a rounded or curved surface around hole 140, to allow locking mechanism 126 to sit relatively lower with respect to connector 122, or for other purposes. Threaded hole 194 is for accommodating threaded portion 172 of sleeve mechanism 124. Suitable break-off nuts may also include those disclosed in U.S. Pat. No. 6,478,795, which is incorporated by reference herein in its entirety. It will be seen that a variety of locking members could be used depending on the configuration of sleeve mechanism 124. For example, a variety of threaded members could be used if sleeve 124 is threaded, or if sleeve 124 is not threaded, other types of locking, holding or clamping members could be used.

A washer 196 is provided in an illustrated embodiment, and can be considered a part of locking mechanism 126. Washer 196 is substantially circular in a particular embodiment, with a hole 198 that may be oblong. Washer 196 may have a curved surface 200 for meeting locking member 190, and a curved surface 202 for meeting connector 122. Surface 200 is convex in one embodiment, having a curvature substantially the same as a surface of locking member 190, so that locking member 190 can slide around or along washer 196 prior to being locked, and so that a maximum amount of surface area of surface 200 and locking member 190 will meet when locked. Surface 202 is convex in a particular embodiment, having a curvature substantially the same as a surface of connector 122, so that washer 196 can slide around or along connector 122 prior to being locked; and so that a maximum amount of surface area of surface 202 and connector 122 will meet when locked. Surfaces 200 and 202, and their counterpart surfaces of locking member 190 and connector 122, may be smooth, roughened or a combination thereof Other embodiments of washer 196 may include flat surfaces and/or different hole sizes or configurations.

Implant 128 is shown in one embodiment as a screw substantially identical to the embodiment of implant 28 shown and described above. Support 130 is shown in one embodiment as a rod substantially identical to the embodiment of support 30 shown and described above. The variations noted above with respect to implant 28 and support 30 are equally applicable to implant 128 and support member 130.

Connector 122, sleeve mechanism 124 and locking mechanism 126 may be loosely assembled at or around the time of manufacture, or at another time prior to surgery. In embodiments that include bulbous member 184, sleeve mechanism 124 is inserted through bulbous member 184 so that protrusion(s) 179 are at least partially within indentation(s) 188. Sleeve mechanism 124 may be slightly compressed from an unstressed state during insertion, and may regain its unstressed state when protrusion(s) 179 enter indentation(s) 188. Bulbous member 184 is thus connected to sleeve mechanism 124 so that they can translate with respect to each other a relatively short distance while not easily disconnected from each other. In particular embodiments in which indentation 188 is a generally annular groove, bulbous member 184 may be able to rotate with respect to sleeve mechanism 124.

Sleeve mechanism 124 is inserted into hole 40 so that a portion of sleeve mechanism 124 extends from connector 22. Locking mechanism 126 is connected to sleeve mechanism 124. In embodiments in which sleeve mechanism 124 and locking mechanism 126 are threaded, locking mechanism 126 is threaded onto sleeve mechanism 124. Locking mechanism 126 is loosely connected to sleeve mechanism 124 so that connector 122, sleeve 124 and locking mechanism 126 can be later adjusted and/or tightened with respect to each other. In one embodiment, one or more connectors 122 can be loaded onto support 130 by inserting support 130 into hole 136 of each such connector 122. Connector(s) 122 can be assembled with respective sleeve(s) 124 and locking mechanism(s) 126 prior to being loaded onto a support 130. Alternatively, connector(s) 122 may be first loaded onto support member 130, and then assembled with respective sleeve(s) 24 and lock(s) 126.

Once such implant(s) (e.g. implants 128) are placed as desired, the surgeon can move support member 130 into position adjacent the implants. An implant such as implant 128 can be connected to support member 130 via a connector 122 with a sleeve 124 and lock 126 loaded thereon. Support member 130 is maneuvered to a position adjacent implant 128, and connector 122 is moved along support 130 so that its hole 140 and hole 178 of sleeve mechanism 124 is adjacent implant 128. Connector 122 is placed over implant 128, so that at least a portion of implant 128 is inside hole 178 of sleeve 124. A portion of implant 128 may also be within hole 140 of connector 128. Connector 122, with sleeve 124 and lock 126, can be moved along implant 128 to the degree desired by the surgeon. Implant 128 can extend somewhat from sleeve mechanism 124 and/or locking mechanism 126, or can be substantially level with sleeve 124 and/or lock 126 (as in FIG. 1), or can be lower than sleeve 124 and/or lock 126, depending on how distant the surgeon wishes connector 122 and support member 130 to be from bone tissue.

When connector 122 is positioned with respect to implant 128 as desired, the surgeon than locks the construct. In the embodiment in which locking mechanism 126 is a nut, it is tightened on sleeve mechanism 124. When locking mechanism 126 tightens against connector 122, sleeve mechanism 124 is pulled through hole 140, so that a portion of sleeve mechanism 124 contacts support 130. In an embodiment having bulbous member 184 or the like, such member may contact support 130. In an embodiment without bulbous member 184, widened portion 176 may contact support 130. In an illustrated embodiment, convex part 186 contacts support member 130 and presses it against connector 122. Tightening also causes compression of sleeve 124 around implant 128 as a reaction to pressing support 130 against connector 122. Apparatus 120 is locked when locking mechanism 126 causes sleeve mechanism 124 to press support 130 against connector 122, with sleeve mechanism 124 being compressed against implant 128. In a locked condition, sleeve 124 is pressed against implant 128 so that relative movement between them is prevented or substantially inhibited, and support 130 is pressed against connector 122 so that relative movement between them is prevented or substantially inhibited.

The disclosed embodiments are not mutually exclusive. That is, aspects of one embodiment can replace aspects of another embodiment, or aspects of one embodiment can be added to or otherwise used in conjunction with another. As examples, sleeve mechanism 124 can be used with the embodiment of apparatus 20 or any other embodiment within the scope of the claims, and the positioning of hole 36 could be used in the embodiment of apparatus 12 or any other embodiment within the scope of the claims. Of course, the disclosed embodiments are not intended to limit in any way the scope of the claims herein. It will be appreciated that the parts of the embodiments shown and described may be made of biocompatible materials such as stainless steel, titanium, ceramics or hard plastics, or other known or developed biocompatible materials.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus comprising:
   an orthopedic implant;
   a support member;
   a connector connecting said implant and said support member, said connector having a first hole for accommodating said support member, said hole having a longitudinal axis along or parallel to said support member, and a second hole in the form of a slot having a long dimension and a short dimension perpendicular to said long dimension, said first and second holes communicating with each other and said long dimension being parallel to said longitudinal axis of said first hole;
   a sleeve member slidable along the outside of said implant and inside said second hole, said sleeve member having a longitudinal axis, a threaded portion at one end, a first convex section and a second convex section having different curvatures extending along said longitudinal axis, said first convex section having a first curvature extending along said longitudinal axis, said second convex section having a second curvature extending along said longitudinal axis that curves at a different rate relative to said first curvature, said sleeve member further including a generally straight medial portion having a smaller outside diameter than said threaded portion positioned between said threaded portion and said first and second convex sections, and at least one slot substantially parallel to said sleeve axis in said generally straight medial portion and said first and second convex sections; and
   a locking member that connects to said sleeve member and adapted to tighten against said connector and cause said first convex section of said sleeve member to contact said support member and force said support member against a portion of said connector, said sleeve member being compressed against said implant with said second convex section of said sleeve member in contact with said connector.

2. The apparatus of claim 1, wherein said connector has a side surface adjacent said second hole, and a plane bisecting said side surface is above said axis of said first hole.

3. The apparatus of claim 1, wherein said connector has a first surface and a second surface through which said second hole extends, said first surface being adjacent said outer surface, said second surface being adjacent said locking member, and said axis of said first hole being closer to said first surface than it is to said second surface.

4. The apparatus of claim 1, wherein said locking member includes a nut.

5. The apparatus of claim 1, wherein said first convex section is nearer to said generally straight medial portion than said second convex section is to said generally straight medial portion, and said first convex section fixedly engages said support member when said apparatus is locked.

6. The apparatus of claim 1, wherein said threaded portion includes two diametrically opposed flat surfaces separating threaded sections.

7. The apparatus of claim 1, wherein said implant has a threaded bone-connecting portion and a smooth cylindrical portion abutting said bone-connecting portion and extending to one end of said implant, said sleeve and said connector being lockable at any place on said cylindrical portion.

8. The apparatus of claim 1, wherein said connector has a first portion that includes said first hole and a second portion that includes said second hole, said first portion having a width along said axis of said first hole, said second portion having a diameter perpendicular to said axis of said second hole, and said diameter of said second portion being larger than said width of said first portion.

9. The apparatus of claim 1, wherein said connector has an upper surface around said second hole that is concave, and said locking member is a nut having a convex underside compatible with said concave surface.

10. The apparatus of claim 1, wherein said first curvature of said first convex section curves at a slower rate relative to said second curvature of said second convex section.

11. The apparatus of claim 1, wherein said first curvature of said first convex section has a first radius, and wherein said second curvature of said second convex section has a second radius different from said first radius.

12. The apparatus of claim 11, wherein said first radius is relatively larger than said second radius.

13. An apparatus comprising:
    an orthopedic implant;
    a support member;
    a connector for connecting said orthopedic implant and said support member, said connector having a first hole with a longitudinal axis for accommodating said support member, and a second hole in the form of an oblong slot having a long dimension and a short dimension perpendicular to said long dimension, said long dimension parallel to said longitudinal axis of said first hole, said oblong slot defined by two substantially cylindrical wall portions and two substantially flat wall portions, said substantially flat wall portions being substantially parallel to said longitudinal axis, said first and second holes communicate with each other via an open area extending through one of said substantially flat wall portions of said oblong slot;

a sleeve mechanism having a hole therethrough adapted to accommodate a portion of said orthopedic implant, wherein said sleeve mechanism includes an upper threaded portion, a medial portion, and a convex portion, wherein said convex portion is configured to fixedly engage said support member through said open area when said apparatus is locked and said medial portion has a smaller outside diameter than said threaded portion and said convex portion; and a locking member configured to lock said apparatus.

14. The apparatus of claim 13, wherein said second hole has a convex surface that contacts said sleeve mechanism when said apparatus is locked.

15. The apparatus of claim 13, wherein said convex portion of said sleeve includes a first convex section having a first curvature and a second convex section having a second curvature that curves at a different rate relative to said first curvature.

16. The apparatus of claim 15, wherein said first curvature of said first convex section curves at a slower rate relative to said second curvature of said second convex section.

17. The apparatus of claim 15, wherein said first curvature of said first convex section has a first radius, and wherein said second curvature of said second convex section has a second radius different from said first radius.

18. The apparatus of claim 17, wherein said first radius is relatively larger than said second radius.

19. The apparatus of claim 15, wherein said first convex section of sleeve member is fixedly engaged against said support member and said second convex section is in contact with said connector when said apparatus is locked.

20. An apparatus comprising:
an orthopedic implant;
a support member;
a connector for connecting said orthopedic implant and said support member, said connector having a first hole with a longitudinal axis for accommodating said support member, and a second hole in the form of an oblong slot having a long dimension and a short dimension perpendicular to said long dimension, said long dimension parallel to said longitudinal axis of said first hole, said oblong slot defined by two substantially cylindrical wall portions and two substantially flat wall portions, said substantially flat wall portions being substantially parallel to said longitudinal axis, said first and second holes communicate with each other via an open area extending through one of said substantially flat wall portions of said oblong slot;
a sleeve mechanism having a hole therethrough adapted to accommodate a portion of said orthopedic implant, wherein said sleeve mechanism includes an upper threaded portion, a medial portion, and a convex portion, wherein said convex portion is configured to fixedly engage said support member through said open area when said apparatus is locked and said medial portion has a smaller outside diameter than said threaded portion and said convex portion; and
a locking member configured to lock said apparatus; and
wherein said second hole has a concave surface that contacts said sleeve mechanism when said apparatus is locked.

* * * * *